(12) United States Patent  (10) Patent No.: US 7,485,126 B2
Adelman et al.  (45) Date of Patent: Feb. 3, 2009

(54) SCALPEL BLADE GUARD

(75) Inventors: Mark Adelman, Short Hills, NJ (US); Robert Landis, Mountainside, NJ (US); Craig Hidalgo, Langhorne, PA (US)

(73) Assignee: New York University, New York, NY (US)

( * ) Notice: Subject to any disclaimer, the term of this patent is extended or adjusted under 35 U.S.C. 154(b) by 1224 days.

(21) Appl. No.: 10/141,349

(22) Filed: May 9, 2002

(65) Prior Publication Data

US 2002/0188309 A1  Dec. 12, 2002

Related U.S. Application Data

(60) Provisional application No. 60/289,518, filed on May 9, 2001.

(51) Int. Cl.
  A61B 17/32 (2006.01)
(52) U.S. Cl. .............................. 606/172; 30/155; 30/286
(58) Field of Classification Search ................. 606/167, 606/170, 172, 185, 184; 30/155, 162
  See application file for complete search history.

(56) References Cited

U.S. PATENT DOCUMENTS

| 1,222,366 A | * | 4/1917 | Curry | 30/286 |
| 1,472,826 A | * | 11/1923 | Champlin | 7/119 |
| 1,599,604 A | * | 9/1926 | Wetmore | 30/156 |
| 2,730,800 A | * | 1/1956 | Bailey | 30/2 |
| 4,736,842 A | | 4/1988 | Uetake et al. | |
| 5,250,064 A | | 10/1993 | Schneider | |
| 5,522,828 A | * | 6/1996 | Malilay | 606/167 |
| 5,741,289 A | * | 4/1998 | Jolly et al. | 606/181 |
| 5,843,107 A | * | 12/1998 | Landis et al. | 606/167 |

FOREIGN PATENT DOCUMENTS

DE  37 22 899  1/1989

* cited by examiner

Primary Examiner—Julian W Woo
Assistant Examiner—Victor X Nguyen
(74) Attorney, Agent, or Firm—Browdy & Neimark, P.L.L.C.

(57) ABSTRACT

A scalpel shield system for a scalpel that has a handle and a blade with a sharp cutting edge. The system is mountable on the scalpel and provided with a blade guard member having a pivot component engagable with a pivot component on the blade or the handle. The blade guard member is manually pivotable relative to the scalpel between a guard position for preventing injury by the sharp cutting edge and a retracted position for exposing the sharp cutting edge.

27 Claims, 8 Drawing Sheets

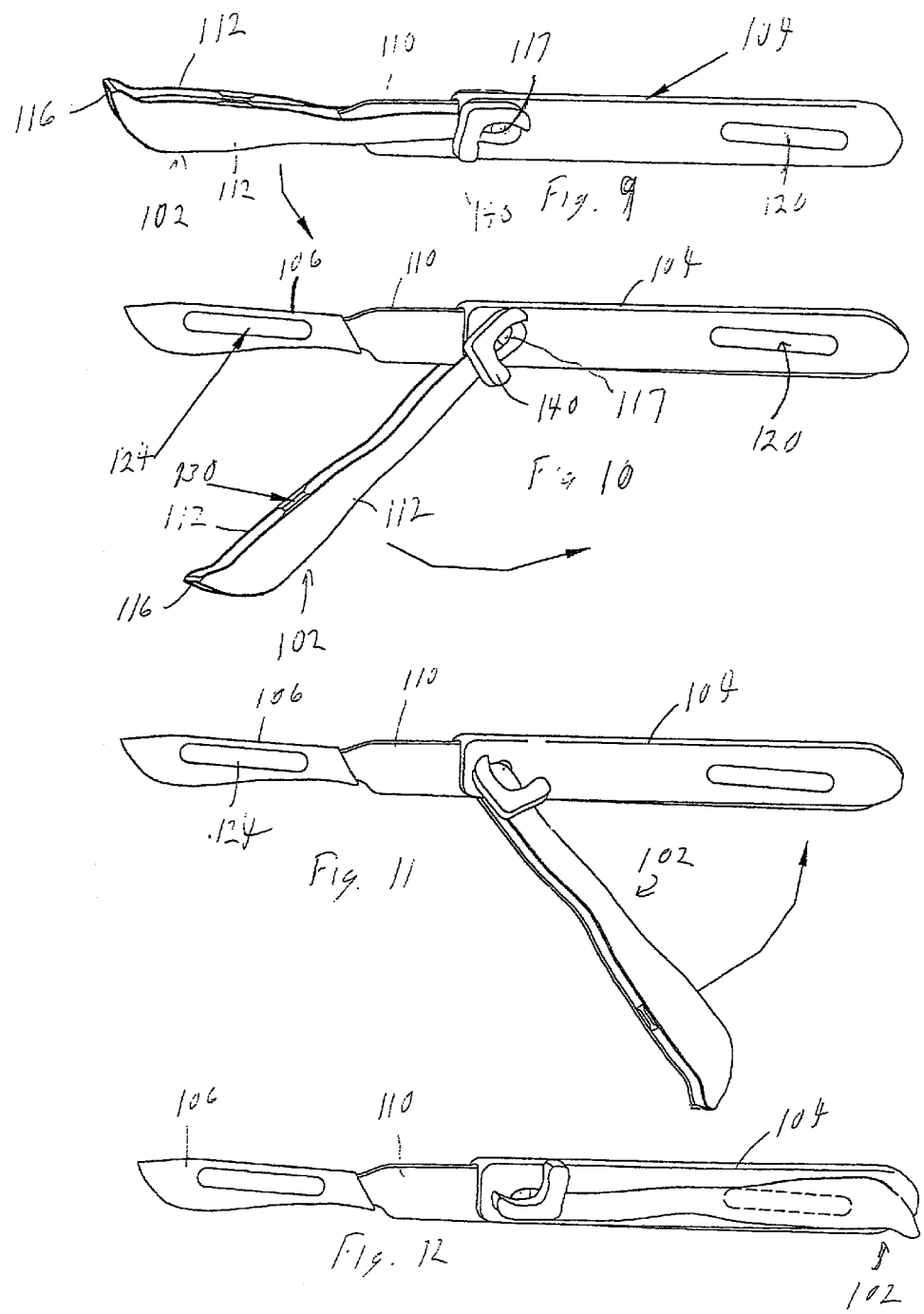

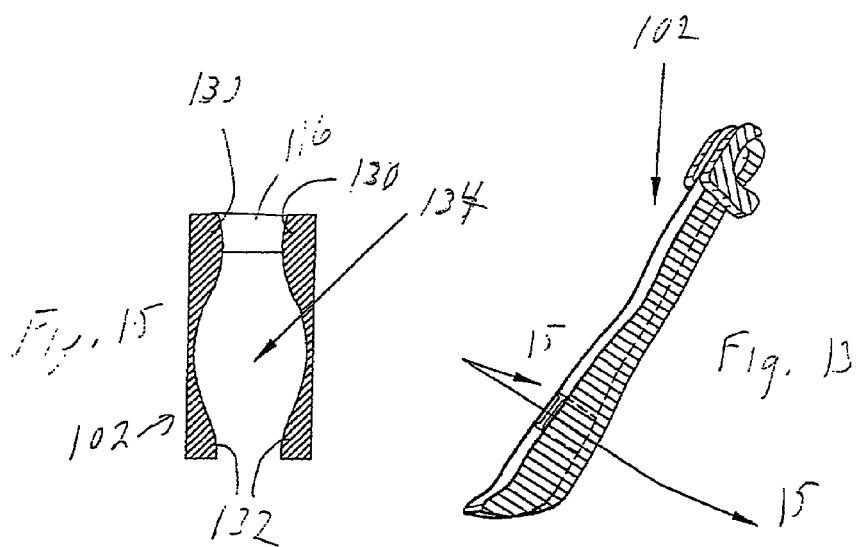
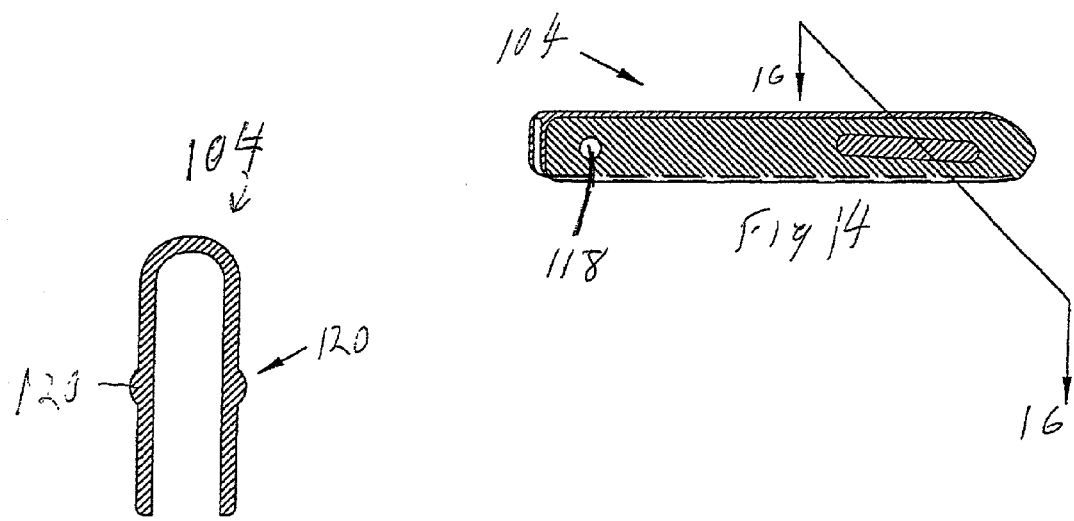

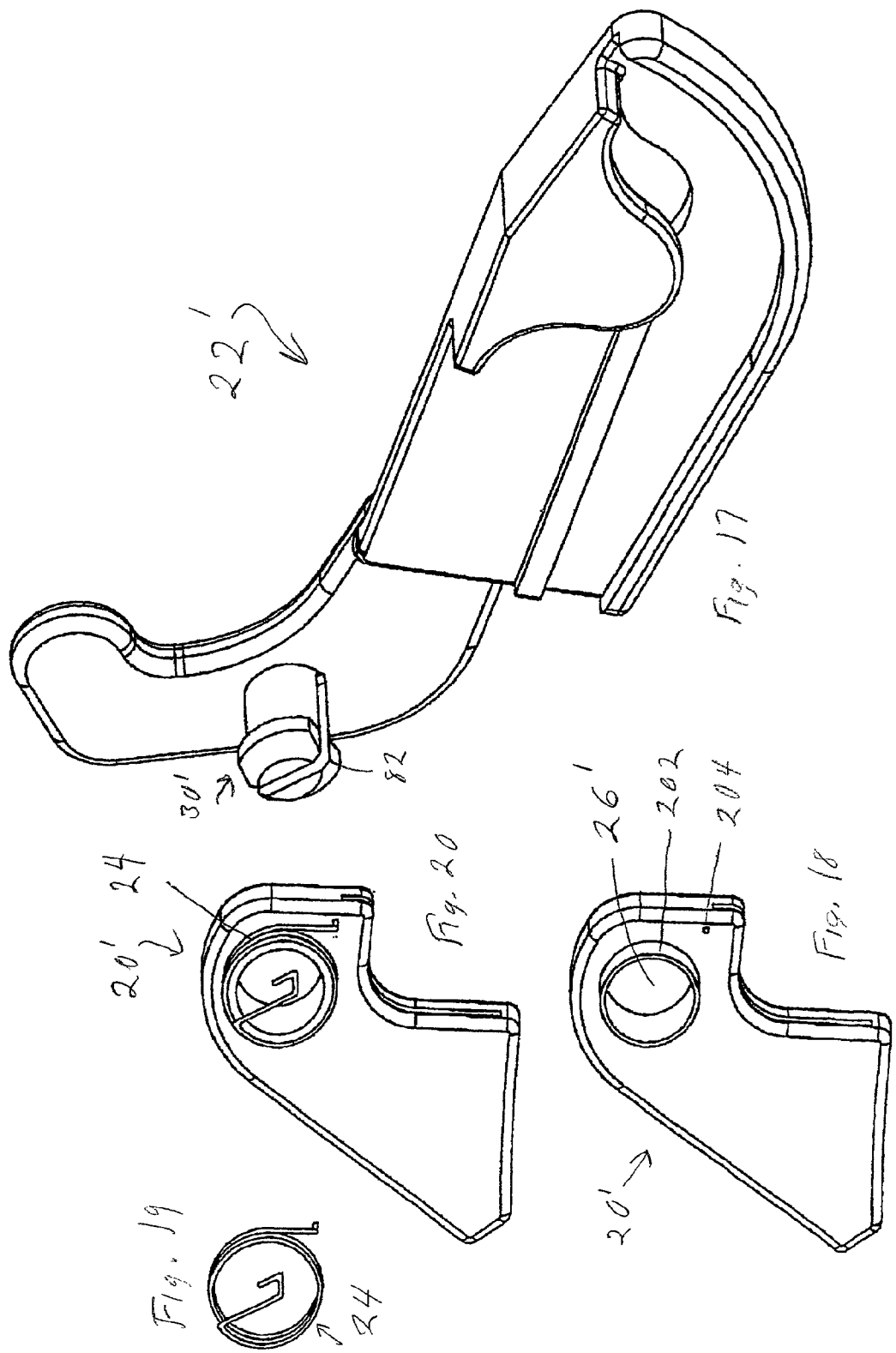

US 7,485,126 B2

SCALPEL BLADE GUARD

This application claims the benefit of U.S. provisional application 60/289,518 filed May 9, 2001.

BACKGROUND OF THE INVENTION

The present invention relates to scalpels, and particularly to arrangements for preventing accidental contact with the cutting edge of the scalpel blade.

A variety of devices of this type, known generally as blade guards, are already known in the art. For example, devices of this type are disclosed in U.S. Pat. Nos. 5,676,677 and 5,843,107, as well as in a number of other issued patents. The known devices are generally capable of only limited movement away from the blade edge, thus placing certain limitations on the use of the scalpel.

BRIEF SUMMARY OF THE INVENTION

The present invention provides an improved scalpel shield system for a scalpel that has a handle and a blade with a sharp cutting edge, the system comprising an adapter mountable on the scalpel and provided with a first pivot component; and a blade guard member having a second pivot component engagable with the first pivot component and manually pivotable relative to the adapter between a guard position for preventing injury by the sharp cutting edge and a retracted position for exposing the sharp cutting edge.

BRIEF DESCRIPTION OF THE DRAWINGS

FIGS. 9-12 are perspective views illustrating a third embodiment of the invention in various operating positions.

FIGS. 13 and 14 are perspective views showing two components of the embodiment shown in FIGS. 9-12.

FIG. 15 is cross-sectional view taken along line 15-15 of FIG. 13.

FIG. 16 is cross-sectional view taken along line 16-16 of FIG. 14.

FIG. 17 is a perspective view of one component of the fourth embodiment of the invention.

FIGS. 18 and 19 are perspective views of second and third components of the fourth embodiment of the invention.

FIG. 20 is a view similar to that of FIG. 18, showing the second and third components assembled together.

DETAILED DESCRIPTION OF THE INVENTION

Figure 1:
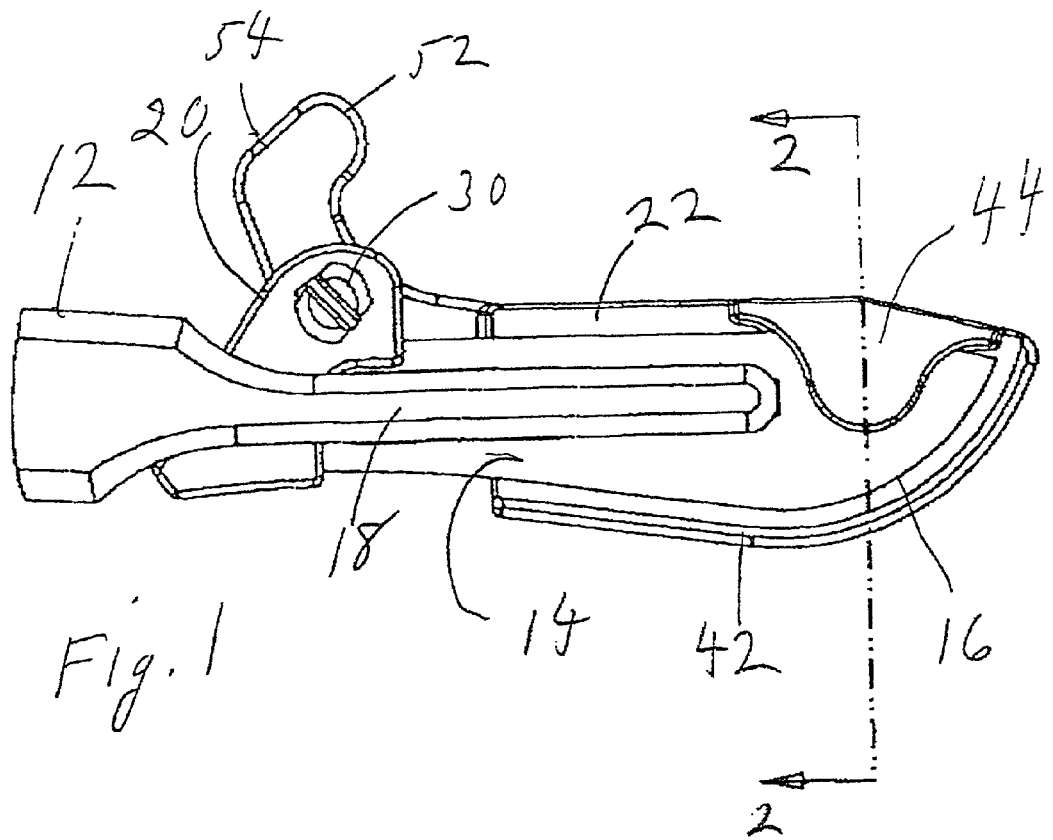
FIG. 1 is a side elevational view illustrating a first embodiment of the invention.
Figure 2:
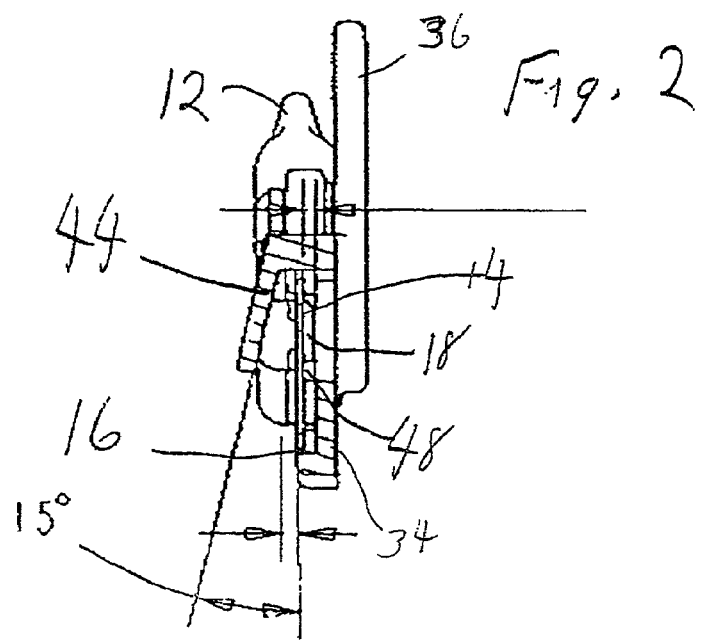
FIG. 2 is a cross-sectional view taken along line 2-2 of FIG. 1.

FIGS. 1 and 2 show a portion of an exemplary scalpel equipped with one preferred embodiment of a scalpel shield system according to the invention. The scalpel is composed of a conventional handle 12, only the distal end of which is shown, and a conventional blade 14 having a cutting edge 16. Handle 12 has a blade supporting member 18 and blade 14 has a mating slot into which supporting member 18 is inserted to hold blade 14 in place on handle 12.

Figure 3:
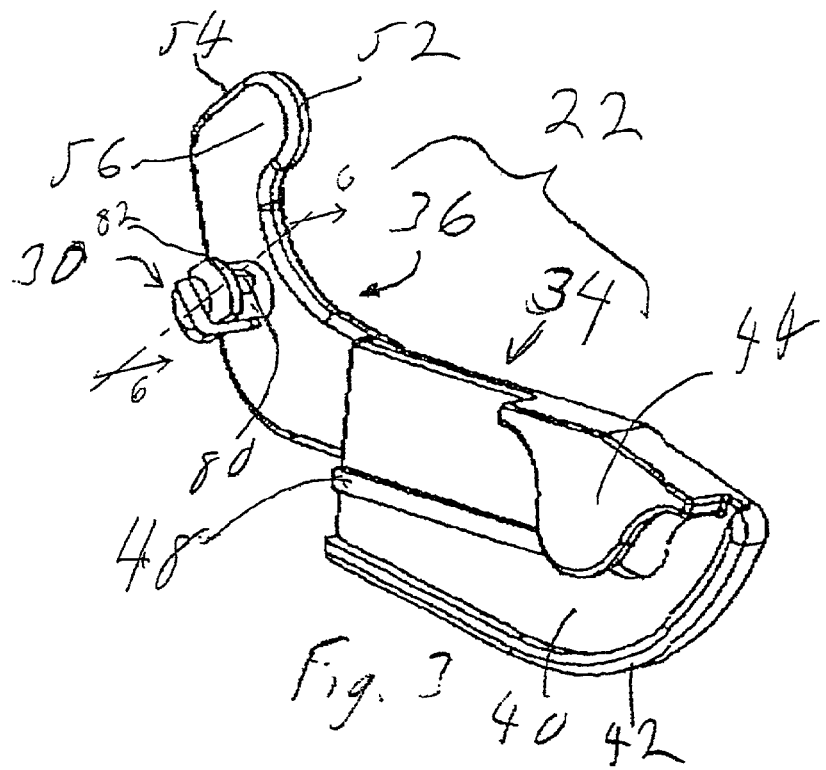
FIG. 3 is a perspective view of one component of the embodiment shown in FIGS. 1 and 2.
Figure 5:
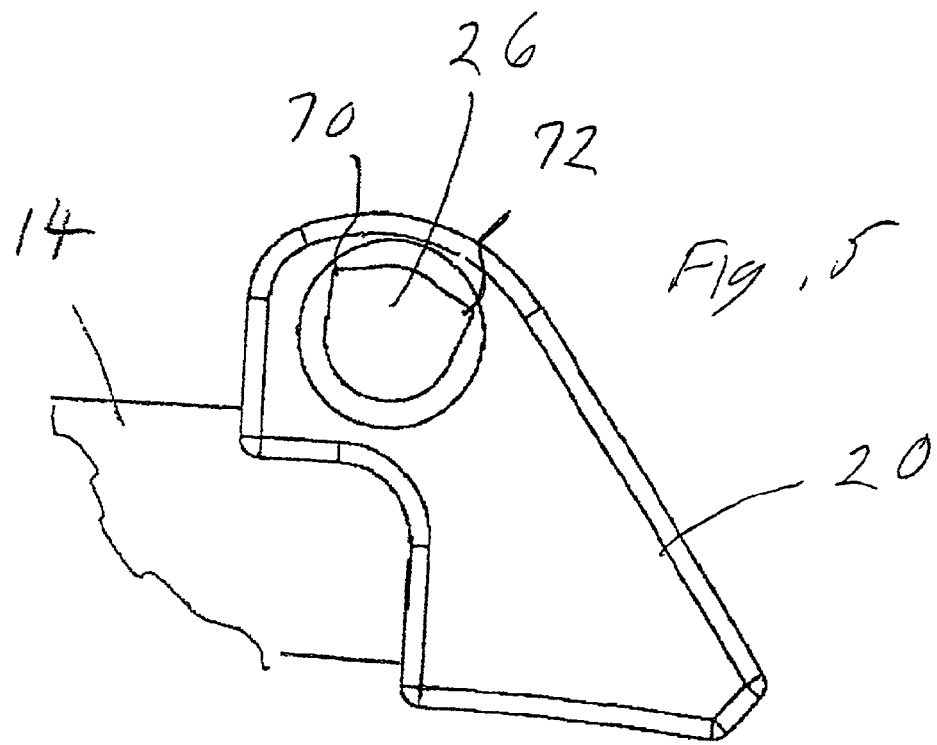
FIG. 5 is a side elevational detail view of a second component of the embodiment of FIGS. 1-4.
Figure 4:
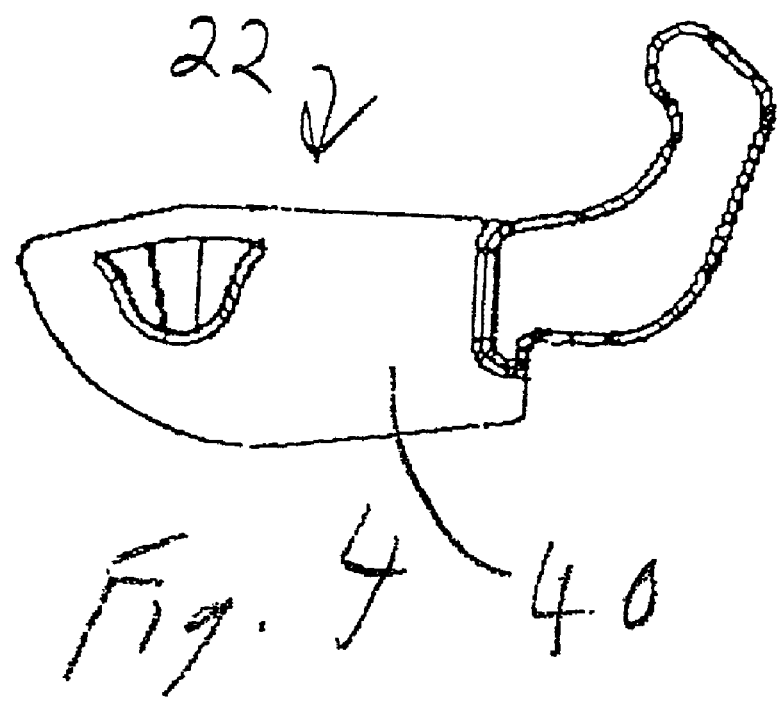
FIG. 4 is a side elevational view of the component shown in FIG. 3, taken in the direction opposite to that of FIG. 3.

The blade guard system according to the invention is composed of two basic parts: an adapter 20 and a blade guard member 22 pivotally mounted on adapter 20, shown in FIGS. 3, 4 and 5. In the illustrated embodiment, adapter 20 is molded around the rear end of blade 14, as shown most clearly in FIG. 5. Alternatively, adapter 20 could be bonded to blade 14 or could be provided with a slot into which blade 14 is force-fitted.

Since adapter 20 is mounted on blade 14, the blade guard assembly can be packaged together with blade 14, with guard member 22 being in the blade guard position shown in FIG. 1. This will then prevent injury when blade 14 is first unpacked and placed on handle 12.

Adapter 20 is provided with a through hole 26, shown in FIG. 5, for receiving a pin 30 that is integral with guard member 22. Guard member 22 is further composed of a blade cover portion 34 and a manually engageable control portion 36 from which pin 30 extends. Pin 30 is slotted along a plane containing the longitudinal axis of the pin.

As will become apparent from the detailed description herein, guard member 22 can pivot through a substantial angle, up to 180°, to fully expose blade 14. Cover portion 34 has a side wall 40, a lower edge carrying a lip 42 and an upper edge carrying a projecting element, or retaining member 44 that helps to retain guard member 22 adjacent blade 14 when member 22 is in the guard position shown in FIGS. 1 and 2, in which lip 42 is located alongside and slightly below cutting edge 16 to prevent any contact with that cutting edge.

The surface of wall 40 that faces blade 14 carries a longitudinally extending, laterally projecting rib 48. As best seen in FIG. 2, blade supporting member 18 and rib 48 cooperate to retain guard member 22 in the guard position. When member 22 is in this position, rib 48 is located directly below a portion of blade supporting member 18 that projects from blade 14 toward side wall 40. Such a portion of blade supporting member 18 is shown in FIGS. 2 and, as element 124, in FIGS. 10-12, which illustrate a third embodiment of the invention. When guard member 22 is pivoted away from the guard position, counterclockwise in FIG. 1, rib 48 is deflected laterally by supporting member 18 to prevent guard member 22 from ever touching cutting edge 16.

Control portion 36 is fixed to cover portion 34 and the two portions 34 and 36 are preferably formed as a unitary molded component. Each basic part 20, 22 of the blade guard system is preferably a molded plastic, the preferred material being polypropylene or polyethylene.

Control portion 36 is shaped to extend away from cover portion 34 and has a generally curved form that is concave toward the free end of guard member 22. The exact shape of control portion 36 can be varied, but should be selected to facilitate the various manipulations to be performed, including moving blade guard member 22 between the guard position shown in FIGS. 1 and 2 and one or more retracted positions, as will be described in greater detail below, and removing guard member 22 completely from adapter 20. All of these manipulations may conveniently be performed with the index finger of the hand holding the scalpel, thereby causing minimum interference with the surgical procedure.

To move guard member 22 away from the guard position, the user, for example a surgeon, can press a surface region 52 of control portion 36, and to move guard member 22 back to the guard position, the user can press on a surface region 54. In situations where it is desired to remove guard member 22 completely, the user need only press on a surface region 56 (FIG. 3) in a direction generally parallel to the axis of rotation of pin 30. Pin 30 and hole 26 are formed, as will be described in greater detail below, to allow pin 30 to snap out of hole 26 in response to pressure applied to surface region 56. Pin 30 and hole 26 will be configured and dimensioned to allow this action to be performed by a level of force that can easily be applied by the user but that is sufficient to avoid inadvertent removal of guard member 22.

As is particularly apparent from a consideration of FIG. 2, adapter 20 can be dimensioned so that the surface thereof that faces control portion 36 is flush with, or projects past, the associated side surface of handle 12. As a result, control portion 36 can be moved past handle 12 and guard member can be pivoted through an angle of up to 180° from the guard position.

Figure 6:
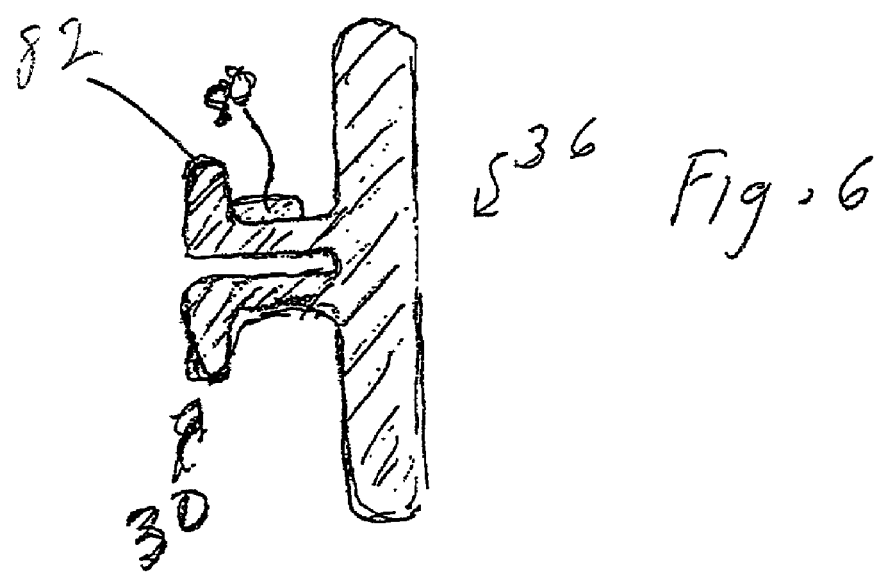
FIG. 6 is a cross-sectional detail view taken along the line 6-6 of FIG. 3.

The functional relation between pin 30 and hole 26 will be described with reference to FIGS. 5 and 6.

Hole 26 has two V-shaped indents, or recesses, 70 and 72 that will cooperate with a rib 80 on pin 30 to define detent positions for guard member 22. Each detent position is defined by engagement of rib 80 in a respective one of indents 70 and 72.

When guard member 22 is in the guard position shown in FIG. 1, rib 80 cooperates with indent 70 to define a first detent position. When guard member has been rotated through an angle of about 135° from the guard position, rib 80 comes to cooperate with indent 72 to define a second detent position. However, the interaction between pin 30 and hole 26 are such that guard member 22 can remain in essentially any angular position when no manual force is being applied. The detent positions are somewhat more stable than the other positions and give the user a tactile sense that guard member 22 is in one of the detent positions.

The free end of pin 30 has a bifurcated rim, or lip, 82 that helps to retain pin 30 in place in hole 26. Rim 82 and the slot in pin 30 are dimensioned, along with the other parts of pin 30, to reliably retain pin 30 in hole 26 while allowing pin 30 to be forced out of hole 26 by the application of an appropriate force to surface region 56.

According to one variation, cover portion 34 can be modified to provide a lock that will hold blade guard member 22 in the guard position.

Figure 7A:
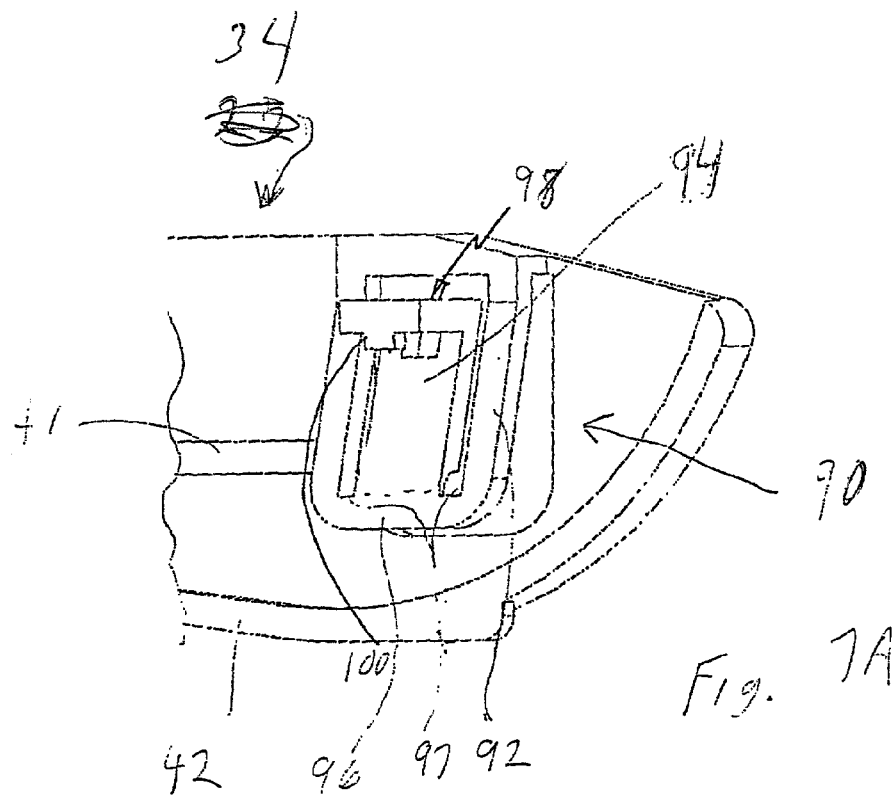
FIGS. 7A and 7B are perspective views, from different directions, of a portion of a blade shield according to a second embodiment of the invention.
Figure 7B:
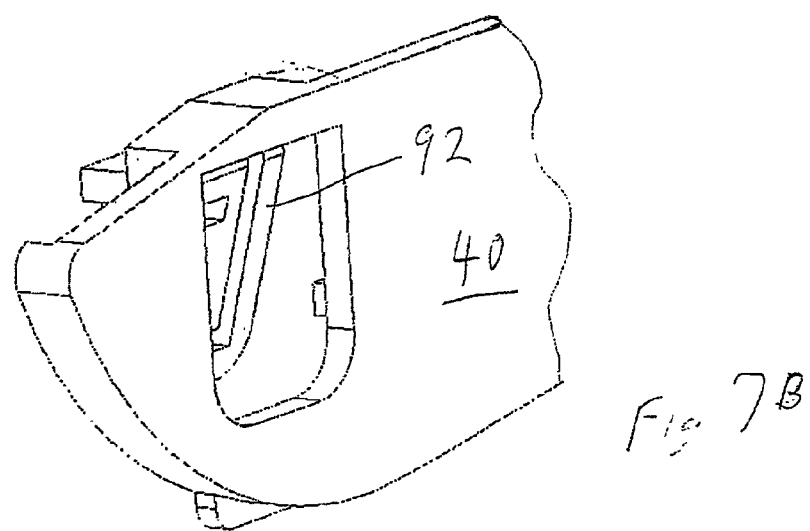
Figure 8:
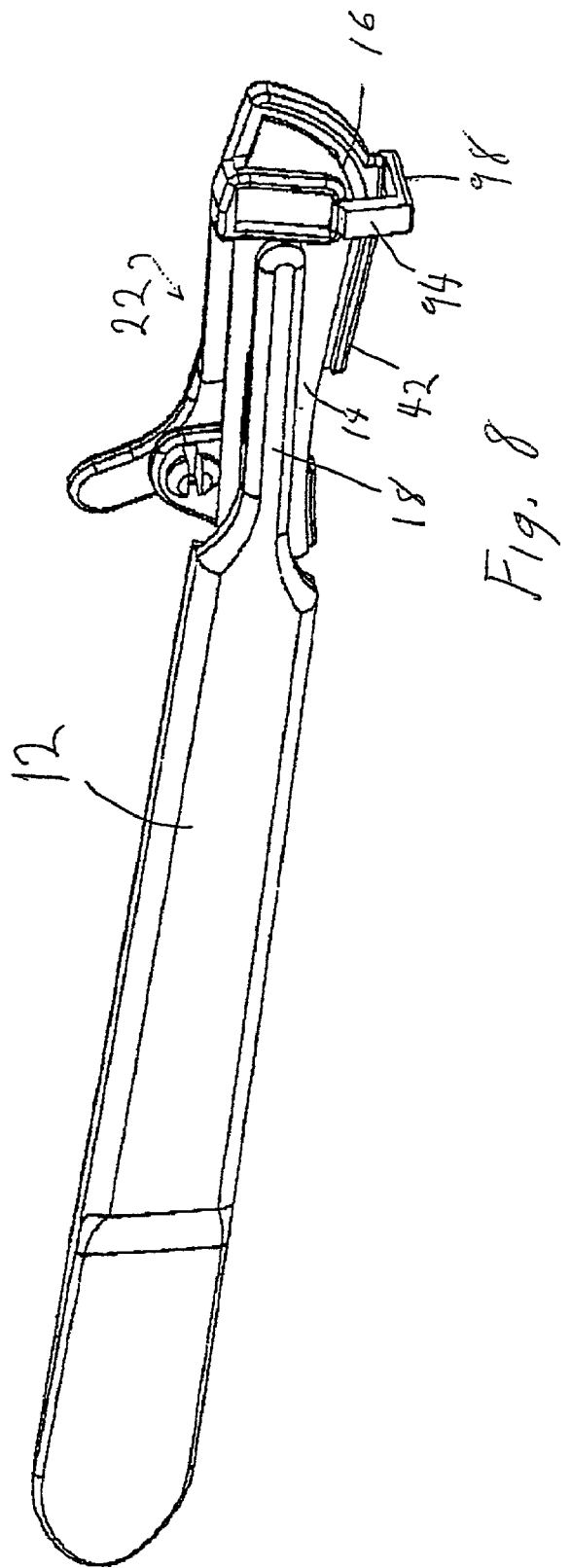
FIG. 8 is a perspective view showing the second embodiment of the invention with its blade shield in a locked position.

One example of such a lock is shown in FIGS. 7A, 7B and 8, where element 44 is replaced by an element 90 that is composed of a support portion 92 and a lock portion 94. Preferably, element 90 is formed as an integral part of blade guard member 22.

Support portion 92 extends from the upper edge of cover portion 34 and performs the same function as element 44. Support portion 92 has the form of a frame and includes a lower frame strip 96.

Lock portion 94 is joined to frame strip 96 along a reduced thickness line that provides an integral hinge 97. The end of lock portion 94 that is remote from frame strip 96 is provided with a laterally projecting leg 98 that carries a latch element, or finger, 100. Lock portion 94 can be manually engaged, at leg 98, and pivoted about hinge 97 to move leg 98 beneath lip 42 so that latch element 100 engages side wall 40. Thus, guard member 22 will be locked in the guard position, as shown in FIG. 8.

FIGS. 7A and 7B further show cutouts included in side wall 40 and lock portion 94 to permit guard member 22 to be molded in one piece.

A third embodiment of a scalpel shield system according to the invention is illustrated in FIGS. 9-16 and differs from the embodiments previously described in that it has a guard member 102 that is secured to a handle sleeve 104, rather than to a blade 106, or blade adapter.

Blade 106 is carried by a scalpel handle 110 in the same manner that blade 14 is carried by blade supporting member 18 of handle 12 in the embodiments of FIGS. 1-8. Specifically, in the embodiment shown in FIGS. 9-16, handle 110 has a blade supporting member with a portion 124 that projects laterally from the blade supporting member and engages a slot in blade 106. Configurations of the slot in blade 106 and of portion 124 to securely but removably hold blade 106 in place are already well known in the art. Handle sleeve 104 is internally configured to be securely but removably attached to handle 110, as for example with elements that provide a snap fit therebetween.

Guard member 102 is composed of two longitudinally extending side members 112 pivotally mounted at the their ends to the forward end of handle sleeve 104 and connected together at their front ends by a web 116.

To provide the pivotal mounting, each side member 112 of guard member 102 is provided with a pin 117 and these pins engage in pin holes 118 in sleeve 104 (see FIG. 14)

Handle sleeve 104 is provided with two protuberances 120, each located at a respective side of sleeve 104. Protuberances 120 extend in the longitudinal direction of handle sleeve 104, starting from a point spaced from the rear end of sleeve 104.

The blade supporting member of handle 110 is provided with a similar pair of protuberances, one of which is constituted by portion 124, extending from each side of blade 106.

The inner walls of side members 112, i.e. the walls that face one another, are provided with detent portions 130, 132 each located adjacent and upper edge or lower edge of a respective member 112. Detent portions 130 are separated from detent portions 132 by narrowed wall portions that form a region 134 having an enlarged width. The structure provided by elements 130, 132 and 134 is located and dimensioned to engage either protuberances 120 when guard member 102 is in a fully retracted position, or protuberances such as 124 when guard member 102 is in the guard position. When guard member 102 is pivoted to its retracted position, detent portions 132 are moved past protuberances 120 until protuberances 120 come to engage in region 134. On the other hand, when guard member 102 is moved to its guard position, detent portions 130 are moved passed protuberances 124 until the latter come to engage in region 134.

Guard member 102 is further provided with control elements 140 having operating surfaces that, like surface regions 52 and 54 of the first embodiment, can be manually engaged by the user's finger to move guard member 102 between its guard position and its retracted position, while the user continues to grasp handle 104.

A fourth embodiment of the invention is illustrated in FIGS. 17-20. It will be noted that this embodiment is generally similar to the first embodiment illustrated in FIGS. 1-5. Therefore, many of the structural features of the fourth embodiment that are identical to those of the first embodiment will not be provided with reference numerals in FIGS. 17-20.

The fourth embodiment is composed essentially of an adapter 20' (FIGS. 18 and 20), a blade guard member 22' (FIG. 17) and a biasing spring 24.

The fourth embodiment differs from the first embodiment essentially in that the through hole 26' of adapter 20' and the outer surface of pin 30' on guard member 22' are essentially circular. Thus, pin 30' is not provided with a rib, such as rib 80 of the first embodiment, but is provided with a rim 82 that serves to retain pin 30' in place in hole 26'. As in the first embodiment, pin 30 is slotted along a plane containing the longitudinal axis the pin.

Adapter 20' is provided with a circularly cylindrical sleeve 202, the outer edge of which will bear against rim 82 when member 22' is assembled to adapter 20'. Therefore, pin 30 is made longer than pin 30 of the first embodiment by an amount equal to the height of sleeve 202.

The fourth embodiment is further provided with a biasing element, which is here in the form of a torsion spring 24. Spring 24 will be seated around sleeve 202 with one end of spring 24 being bent to be seated in a post hole 204 provided in adapter 20'. Then, when pin 30' is inserted through hole 26 with an orientation corresponding to the blade guard position, the opposite end of spring 24 will slide into the slot provided in pin 30'. During insertion of pin 30 into hole 26, the two halves of pin 30' will be deflected toward one another to allow passage of rim 82. When pin 30' has been fully inserted, its two halves will snap outwardly so that rim 82 will bear against the outer edge of sleeve 202. Rim 82 is also preferably dimensioned to cover spring 24 and thus to retain spring 24 in position. Pin 30', adapter 20', and sleeve 202 will be dimensioned to eliminate any noticeable play between adapter 22 and guard member 22' in the direction parallel to the longitudinal axis of pin 30'. In addition, pin 30' is dimensioned to fit snugly in hole 26' to assure that guard member 22' will pivot relative to adapter 20' over a precisely defined path, thereby assuring that when guard member 22' is moved to its blade guard position, it will properly engage the scalpel blade.

Spring 24 is configured and dimensioned to bias guard member 22' toward and into the blade guard position. Therefore, guard member 22' must be actively held in its retracted position by the user. When the user releases guard member 22 it will automatically pivot into the guard position.

It should be readily apparent that a biasing member can also be incorporated into the other embodiments disclosed herein and that the biasing member can have a form other than a torsion spring.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A scalpel shield system for a scalpel that has a handle and a blade with a sharp cutting edge, said system comprising:
   an adapter mountable on the scalpel and provided with a first pivot component; and
   a blade guard member having a second pivot component engagable with said first pivot component and manually pivotable relative to said adapter about a pivot axis between a guard position for preventing injury by the sharp cutting edge and a retracted position for exposing the sharp cutting edge, said blade guard member remaining in either position in the absence of a positive manual activation, wherein said pivot components contact one another, are concentric to the pivot axis, and one of said pivot components is provided with a recess and the other of said pivot components is provided with a rib, said rib and said recess interacting to define at least one detent position of said blade guard member relative to said adapter.

2. The system of claim 1 wherein said adapter is constructed to be mounted on the blade.

3. The system of claim 1 wherein the handle has a blade supporting portion that engages the blade and projects laterally from the blade, and said blade guard member has a raised portion that interacts with said blade supporting portion to maintain said guard member out of contact with the sharp cutting edge during movement for said blade guard member from the guard position.

4. The system of claim 1 wherein said blade guard member has a main portion provided with a protective edge that extends along one side of the blade when said blade guard member is in the guard position.

5. The system of claim 4 wherein said blade guard member has a retaining member that extends along the side of the blade that is opposite to the one side to retain said main portion of said blade guard member adjacent the blade when said blade guard member is in the guard position.

6. The system of claim 1 wherein said blade guard member comprises a locking element movable to lock said blade guard member in the guard position.

7. The system of claim 1, further comprising a spring element connected between said adapter and said blade guard to produce a force that biases said blade guard toward the guard position.

8. The system of claim 7 wherein said spring element is a torsion spring.

9. The system of claim 1 wherein said recess is V-shaped.

10. The system of claim 1, wherein said blade guard member comprises a blade cover portion and a manually engageable control portion that is fixed to said blade guard portion and that extends away from said blade cover portion, said control portion being manually actuatable to move said blade cover portion between the guard position and the retracted position.

11. A scalpel shield system for a scalpel that has a handle and a blade with a sharp cutting edge the handle having a blade supporting that engages the blade and projects laterally from the blade, said system comprising:
    an adapter mountable on the scalpel and provided with a first pivot component; and
    a blade guard member having a second pivot component engagable with said first pivot component and manually pivotable relative to said adapter between a guard position for preventing injury by the sharp cutting edge and a retracted position for exposing the sharp cutting edge, said blade guard member being manually pivotable relative to said adapter through an angle of substantially 180°, wherein said blade guard member has a raised portion that is constructed to interact with the blade supporting portion to maintain said guard member out of contact with the sharp cutting edge during movement of said blade guard member from the guard position.

12. The system of claim 11 wherein said adapter is constructed to be mounted on the blade.

13. The system of claim 11 wherein said pivot components are shaped to define at least one detent position of said blade guard member relative to said adapter.

14. The system of claim 11 wherein said blade guard member has a main portion provided with a protective edge that extends along one side of the blade when said blade guard member is in the guard position.

15. The system of claim 11 wherein said blade guard member comprises a locking element movable to lock said blade guard member in the guard position.

16. The system of claim 11 further comprising a spring element connected between said adapter and said blade guard to produce a force that biases said blade guard toward the guard position.

17. The system of claim 16 wherein said spring element is a torsion spring.

18. A scalpel shield system for a scalpel that has a handle and a blade with a sharp cutting edge, said system comprising:
- an adapter mountable on the scalpel and provided with a first pivot component; and
- a blade guard member having a second pivot component engagable with said first pivot component and manually pivotable relative to said adapter between a guard position for preventing injury by the sharp cutting edge and a retracted position for exposing the sharp cutting edge, said blade guard member being manually pivotable relative to said adapter through an angle of substantially 180°, wherein said blade guard member has a main portion provided with a protective edge that extends along one side of the blade when said blade guard member is in the guard position, and wherein said blade guard member has a retaining member that extends along the side of the blade that is opposite to the one side to retain said main portion of said blade guard member adjacent the blade when said blade guard member is in the guard position.

19. A scalpel shield system for a scalpel that has a handle and a blade with a sharp cutting edge, said system comprising:
- an adapter constructed to be assembled to the blade and provided with a first pivot component; and
- a blade guard member having a second pivot component engagable with said first pivot component and manually pivotable relative to said adapter about a pivot axis between a guard position for preventing injury by the sharp cutting edge and a retracted position for exposing the sharp cutting edge, wherein said pivot components contact one another, are concentric to the pivot axis, and one of said pivot components is provided with a recess and the other of said pivot components is provided with a rib, said rib and said recess interacting to define at least one detent position of said blade guard member relative to said adapter.

20. The system of claim 19 wherein the handle has a blade supporting portion that engages the blade and projects laterally from the blade, and said blade guard member has a raised portion that interacts with said blade supporting portion to maintain said guard member out of contact with the sharp cutting edge during movement for said blade guard member from the guard position.

21. The system of claim 19 wherein said blade guard member has a main portion provided with a protective edge that extends along one side of the blade when said blade guard member is in the guard position.

22. The system of claim 21 wherein said blade guard member has a retaining member that extends along the side of the blade that is opposite to the one side to retain said main portion of said blade guard member adjacent the blade when said blade guard member is in the guard position.

23. The system of claim 19 wherein said blade guard member comprises a locking element movable to lock said blade guard member in the guard position.

24. The system of claim 19 further comprising a spring element connected between said adapter and said blade guard to produce a force that biases said blade guard toward the guard position.

25. The system of claim 24 wherein said spring element is a torsion spring.

26. The system of claim 19 wherein said recess is V-shaped.

27. The system of claim 19, wherein said blade guard member comprises a blade cover portion and a manually engageable control portion that is fixed to said blade guard portion and that extends away from said blade cover portion, said control portion being manually actuatable to move said blade cover portion between the guard position and the retracted position.

* * * * *